US006286507B1

(12) United States Patent
Jahnsson

(10) Patent No.: US 6,286,507 B1
(45) Date of Patent: *Sep. 11, 2001

(54) SINGLE DOSE INHALER I

(75) Inventor: Magnus Jahnsson, Södertälje (SE)

(73) Assignee: Astra Aktiebolag, Sodertalje (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/029,875

(22) PCT Filed: Jan. 29, 1998

(86) PCT No.: PCT/SE98/00129

§ 371 Date: Mar. 2, 1998

§ 102(e) Date: Mar. 2, 1998

(87) PCT Pub. No.: WO98/34661

PCT Pub. Date: Aug. 13, 1998

(30) Foreign Application Priority Data

Feb. 7, 1997 (SE) .................................... 9700421

(51) Int. Cl.⁷ .................................... A61M 15/00
(52) U.S. Cl. ................ 128/203.15; 128/203.21; 128/203.23
(58) Field of Search ........... 128/203.12, 203.15, 128/203.21, 203.23, 203.24, 200.18

(56) References Cited

U.S. PATENT DOCUMENTS

| 2,642,063 | * | 6/1953 | Brown | 128/203.15 |
| 3,795,244 | * | 3/1974 | Lax et al. | 128/203.15 |
| 4,368,850 | * | 1/1983 | Szekely | 128/200.22 |
| 5,437,271 | | 8/1995 | Hodson et al. | 128/203.15 |
| 5,483,954 | * | 1/1996 | Mecikalski | 128/203.15 |
| 5,533,505 | * | 7/1996 | Kallstrand et al. | 128/203.15 |
| 5,676,130 | * | 10/1997 | Gupte et al. | 128/203.15 |
| 5,699,789 | * | 12/1997 | Hendricks | 128/203.15 |
| 5,724,959 | * | 3/1998 | McAughey et al. | 128/203.15 |

FOREIGN PATENT DOCUMENTS

| 2248400 | * | 4/1992 | (GB) | 128/203.15 |
| WO93/17728 | | 9/1993 | (WO) . | |
| WO97/05918 | | 2/1997 | (WO) . | |

* cited by examiner

Primary Examiner—John G Weiss
Assistant Examiner—V. Srivastava
(74) Attorney, Agent, or Firm—Fish & Richardson P.C.

(57) ABSTRACT

A disposable inhaler that includes a deagglomeration section is disclosed. The deagglomeration section has a section inlet, a section outlet, and a divider for splitting the stream of air into two flow parts. The divider has a surface that faces the section inlet at an angle substantially perpendicular to the stream of air passing through the section inlet, and the walls of the inhalation channel within the inhaler are shaped so as to cause substantially no resistance to or turbulence in the air flow through the inhaler.

19 Claims, 7 Drawing Sheets

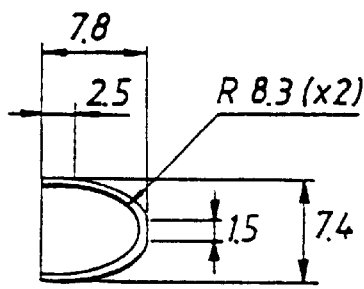
FIG. 10D
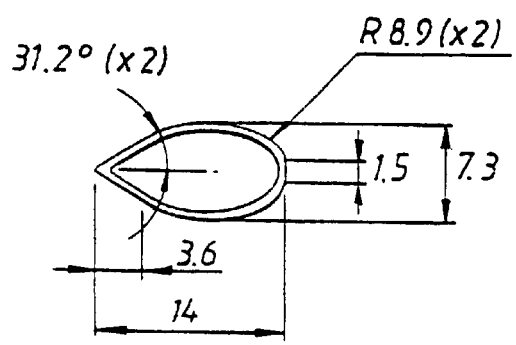
FIG. 10C
FIG. 10B
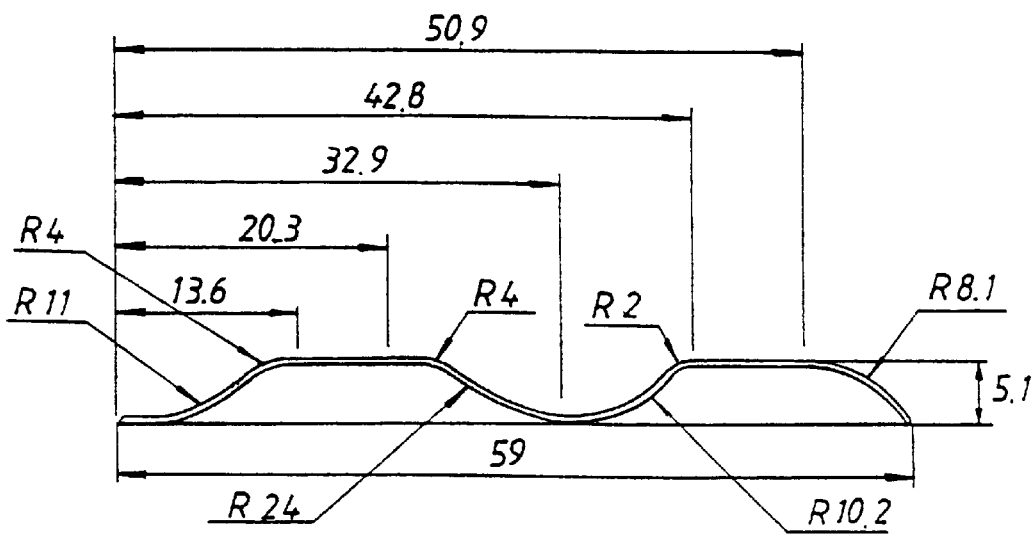
FIG. 11

SINGLE DOSE INHALER I

BACKGROUND

The present invention relates to a disposable inhaler, particularly for administering powder by inhalation.

Previously, as described in WO93/17728 and illustrated in FIGS. 1 to 3 of the accompanying drawings, there was known a disposable inhaler constructed from two parts 1 and 2. The lower part 2 includes a recesses 3 in which a dose of powder is stored and the two parts together define a channel through which a stream of air may be drawn by a user from an air inlet 4 to a mouthpiece 5. A tape 6 is provided to cover the recesses 3 and is additionally bent around the outside of the part 2 to cover an aperture 8 in the bottom of the recess 3. In use, the tape 6 is pulled away from the lower part 2 so as to expose both the aperture 8 and the recess 3. Projections 7 are provided to keep the loose tape out of the way of the air flow and a depression 9 directs the air flow to pick up the powder in the recess 3 more effectively. The channel defined by parts 1 and 2 also includes a deagglomeration section 10 having a section inlet 11, a section outlet 12 and a divider 13. The divider 13 splits the stream of air into two flow paths and powder is caused to impact on internal surfaces. In this way, powder is effectively deagglomerated.

In use, a patient inhales through the mouthpiece 5 causing an air stream to pick up the powder stored in recess 3. As the air/powder mixture flows through the inhaler, powder is deagglomerated then passes out of the mouthpiece 5 and into the lungs of the patient.

SUMMARY OF THE INVENTION

An object of the present invention is to provide improved deagglomeration of powder, in other words to increase the fine particle fraction and fine particle dose.

Another object of the present invention is to minimize retention of powder within the inhaler.

With regard to these two objects, the prior art of FIGS. 1 to 3 included an inhalation channel which directed the air flow along a path with walls that change direction. The changes in the direction of the walls results in powder impacting with those walls and a generally turbulent air flow which assists in deagglomeration of powder.

The present invention is based on the realization that the effects of deagglomeration of powder by the channelling surfaces or any of the surfaces facing downstream of the surfaces of the divider 13 are relatively insignificant.

According to the present invention there is provided an inhaler for administering powder by inhalation, the inhaler comprising:

a channel through which a stream of air may be drawn by inhalation of a user; and a powder dispenser for providing said powder in said stream of air for inhalation by the user; wherein said channel includes at least one deagglomeration section with a section inlet, a section outlet downstream of said section inlet and a divider between said section inlet and said section outlet for dividing said stream of air either side of said divider; and wherein said divider has a surface opposite said section inlet and said surface is oriented at an angle substantially perpendicular to the flow of said stream of air passing through said section inlet.

In this way, powder carried in the air stream is more effectively deagglomerated and the final air/powder mixture inhaled by the user has a higher fine particle fraction and fine particle dose. By providing a perpendicular surface to the divider, there is greater impact of powder with the surface of the divider causing improved deagglomeration throughout the air/powder mixture. Furthermore, impact of the powder with the surface of the divider, together with the air flow past the surface prevents undue retention of powder on the surface. When a large powder particle impacts with the surface, it breaks into smaller particles which rebound back into the airflow and are carried on through the inhaler by that air flow.

Preferably, the surface of the divider extends over at least the area corresponding to a projection of the section inlet on to said divider.

By providing a perpendicular surface over the entire width of the section inlet, the effects and advantages discussed above are maximised.

According to the present invention there is also provided an inhaler for administering powder by inhalation, the inhaler comprising:

a channel through which a stream of air may be drawn by inhalation of a user; and a powder dispenser for providing said powder in said stream of air for inhalation by the user; wherein said channel includes at least one deagglomeration section with a section inlet, a section outlet downstream of said section inlet and a divider between said section inlet and said section outlet for dividing said stream of air either side of said divider, said divider having a surface substantially opposite said section inlet for dividing the air flow entering through said section inlet and affecting deagglomeration of powder in the air flow; and wherein surfaces of the at least one deagglomeration section are shaped and spaced apart so as substantially not to cause any restriction to or turbulence in the stream of air through the inhaler.

According to the present invention, it has been recognized that most of the deagglomeration occurs on the surface of the divider opposite the section inlet and that, with the same size of inhaler and same fine particle fraction/dose, the shape of the walls defining the channel through the inhaler may be modified to reduce the flow resistance and retention of the inhaler.

In particular, with a particular shape and size of divider surface opposite the section inlet for deagglomeration of powder, the remaining surfaces of the deagglomeration section should be shaped to follow the natural flow path of the air deflected either side of the divider. Clearly, this results in reduced deagglomeration effects in the rest of the inhaler other than the deagglomeration surface. However, as mentioned above, the present invention recognizes that the effects of deagglomeration in these parts are relatively insignificant. The advantages of the present invention are that, with reduced disturbance, restriction, turbulence etc. of the stream of air, there is less opportunity for powder to be deposited in the inhaler and the flow resistance experienced by the user inhaling through the inhaler is minimized.

Each section inlet may be fed by one or more substantially straight sections or channels.

The advantage of this is that the powder particles carried in the stream of air then have a well defined momentum towards the facing surface of the deagglomeration divider. This maximizes the number of larger powder particles which leave the direction of flow of the stream of air and which continue straight on to impact with the divider.

Preferably, two deagglomeration sections are provided with the section outlet of one deagglomeration section being in fluid connection with the section inlet of the other deagglomeration section.

The channels formed either side of the divider of one deagglomeration section may feed directly into the section inlet of the next deagglomeration section or they may first join to form a single straight section feeding that section inlet.

The use of two deagglomeration sections provides further improvement in deagglomeration with further increases in the fine particle fraction and fine particle dose. In particular, the fine particles in the air/powder mixture will be carried by the airstream around the surface of the divider. However, those larger heavier particles which escaped deagglomeration by the first divider will have sufficient momentum to leave the flow of air and impact with the surface of the second divider. As with the first divider, the particles break into smaller particles which rebound back into the airstream and are carried on through the inhaler. Of course, the exact shape and size of the second deagglomeration section may differ from that of the first deagglomeration section.

According to the present invention, there is also provided a method of optimizing the characteristics of an inhaler including a channel through which a stream of air may be drawn by inhalation of a user and a powder dispenser for providing said powder in said stream of air for inhalation by the user, said channel including at least one deagglomeration section with a section inlet, a section outlet downstream of said section inlet and a divider between said section inlet and said section outlet for dividing said stream of air either side of said divider, the method comprising:

providing a surface for deagglomeration of the powder on the divider opposite said section inlet and extending over an area corresponding to a projection of the section inlet onto said divider; and choosing dimensions for the rest of the deagglomeration section which cause substantially no restriction to or turbulence in the stream of air through the inhaler.

According to the present invention, there is also provided a method of optimizing the characteristics of an inhaler including a channel through which a stream of air may be drawn by inhalation of a user and a powder dispenser for providing said powder in said stream of air for inhalation by the user, the method comprising:

shaping and sizing the channel so as to cause substantially no restriction to or turbulence in the stream of air in the channel; and causing the channel to change direction with a sufficient angle such that the momentum of particles of powder in the air stream requiring deagglomeration will cause the particles to leave the air flow and impact walls of the channel.

According to the present invention, there is also provided a method of providing deagglomerated powder at the outlet of a channel guiding a stream of air, the channel including at least one deagglomeration section with a section inlet, a section outlet downstream of said section inlet and a divider between said section inlet and said section outlet for dividing said stream of air either side of said divider, the method comprising:

providing powder in said channel upstream of said section inlet; and providing a surface on said divider which is opposite said section inlet and which is orientated at an angle substantially perpendicular to the flow of the stream of air passing through said section inlet.

According to the present invention, there is also provided a method of providing deagglomerated powder at the outlet of a channel guiding a stream of air, the channel including at least one deagglomeration section with a section inlet, a section outlet downstream of said section inlet and a divider between said section inlet and said section outlet for dividing said stream of either side of said divider, said divider having a surface substantially opposite said section inlet for dividing the air flow entering through said section inlet and affecting deagglomeration of powder in the air flow, the method comprising:

providing powder in the channel upstream of said section inlet; and shaping and spacing the surfaces of the channel so as substantially not to cause any restriction to or turbulence in the stream of air through the inhaler.

Medicaments suitable for administration by using the present invention are any which may be delivered by inhalation. Suitable inhalable medicaments may include for example β2-adrenoreceptor agonists for example salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators for example ipratropium bromide and the like; glucocorticosteroids for example beclomethasone, fluticasone, budesonide, tipredane, dexamethasone, betamethasone, fluocinolone, triamcinolone acetonide, mometasone, and the like, and their pharmacologically acceptable esters and salts; anti-allergic medicaments for example sodium cromoglycate and nedocromil sodium; expectorants; mucolytics; antihistamines; cyclooxygenase inhibitors; leukotriene synthesis inhibitors; leukotriene antagonists, phospholipase-A2 (PLA2) inhibitors, platelet aggregating factor (PAF) antagonists and prophylactics of asthma; antiarrhythmic medicaments, tranquilisers, cardiac glycosides, hormones, antihypertensive medicaments, antidiabetic- antiparasitic- and anticancer-medicaments, sedatives and analgesic medicaments, antibiotics, antirheumatic medicaments, immunotherapies, antifungal and antihypotension medicaments, vaccines, antiviral medicaments, proteins, polypeptides and peptides for example peptide hormones and growth factors, polypeptides vaccines, enzymes, endorphines, lipoproteins and polypeptides involved in the blood coagulation cascade, vitamins and others, for example cell surface receptor blockers, antioxidants, free radical scavengers and organic salts of N,N'-diacetylcystine.

The present invention will be more clearly understood from the following description, given by way of example only, with reference to the accompanying drawings.

BRIEF DESCRIPTION OF THE DRAWINGS

FIGS. 10(a) to (d) illustrate the dimensions of the channel section of FIG. 9;

FIG. 11 illustrates the flow path through half of the channel section of FIG. 9;

DETAILED DESCRIPTION OF THE PREFERRED EMBODIMENTS

Figure 5:
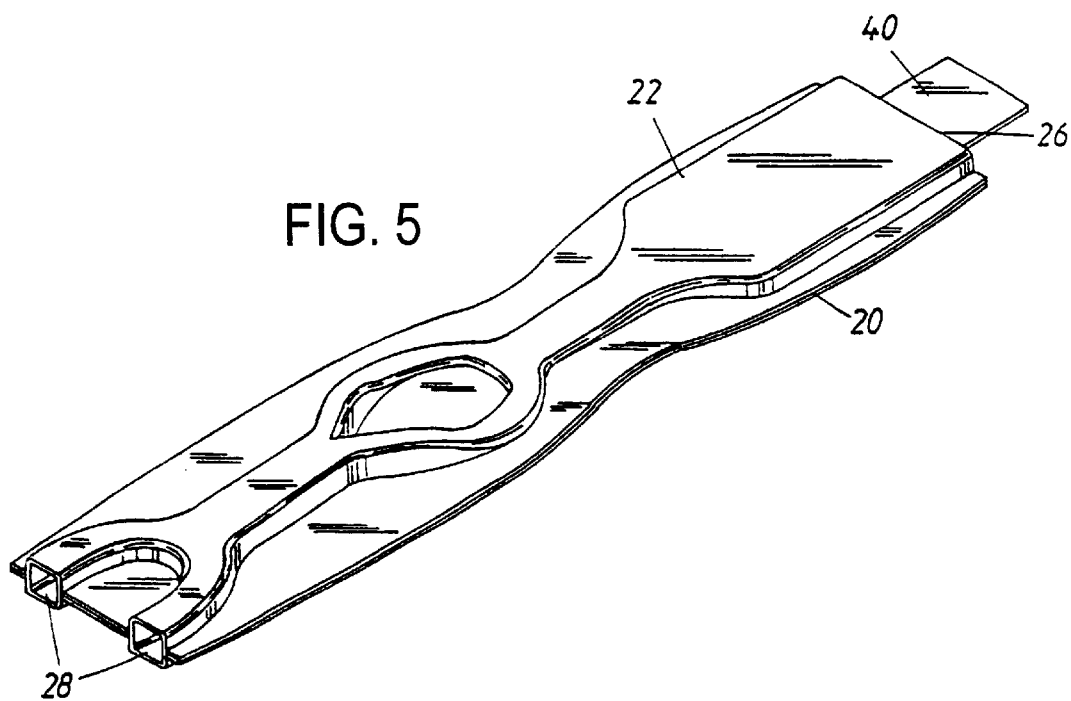
FIG. 5 illustrates an inhaler according to the present invention.
Figure 6:
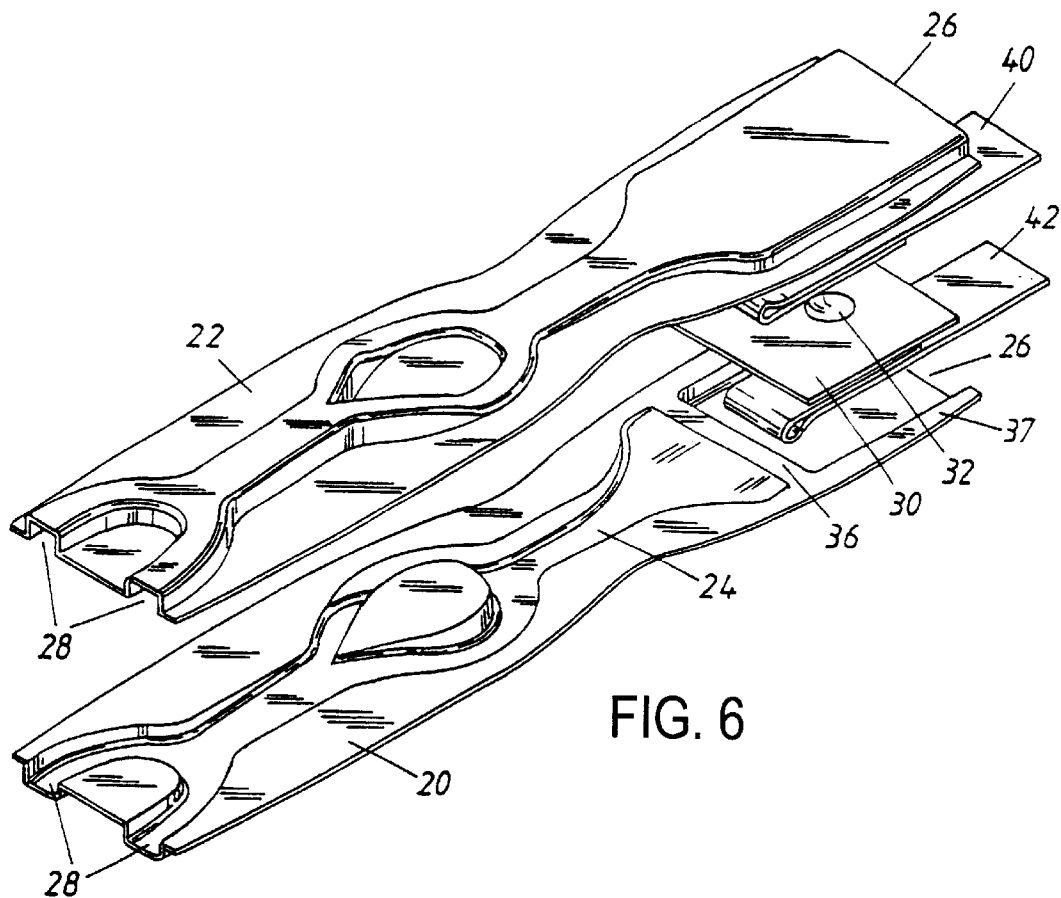
FIG. 6 illustrates the inhaler of FIG. 5 separated into its component parts.
Figure 7:
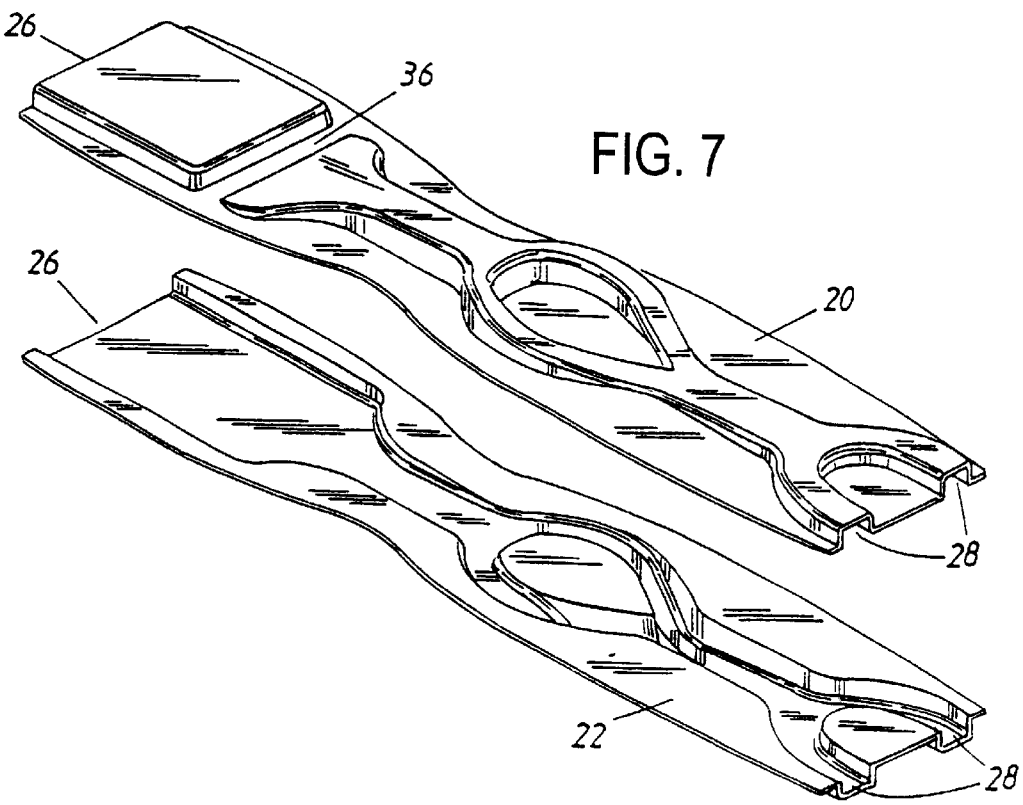
FIG. 7 illustrates the main two parts of FIG. 5 from below.

As illustrated in FIGS. 5, 6 and 7, the inhaler is constructed from a first part 20 and a second part 22 which together define an inhalation channel 24 joining an air inlet 26 and an outlet 28. In this illustrated embodiment, the outer shape of the inhaler corresponds to the inner channelled shape. Clearly, however, this is not necessary and the outer shape may take any other form.

At an inlet end of the inhaler, a plate 30 is provided. The plate 30 has a depression 32 in which a dose of powder is stored. The use of a separate plate 30 in which the depression 32 is formed is particularly advantageous, since it allows the depression 32 to be made from a material different from that of the two parts 20 and 22. In particular, it is advantageous to make the depression 32 from a strong water impermeable material such as aluminium or aluminium laminate, whereas the first and second parts 20 and 22 may be constructed of transparent plastics material, such that the inhalation channel maybe inspected before and after use.

Figure 8:
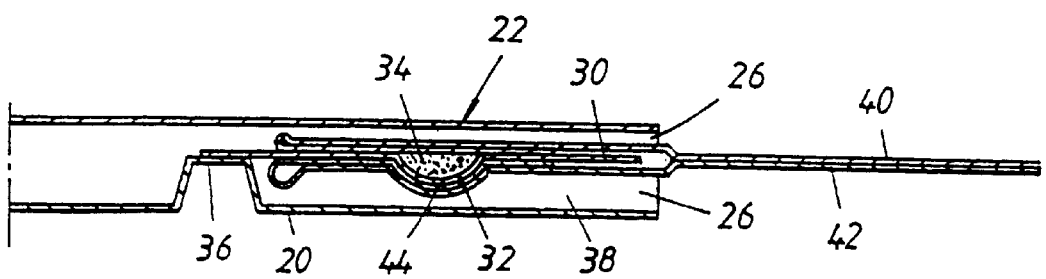
FIG. 8 illustrates a cross-section of the inlet of the inhaler of FIG. 5.

As illustrated in FIG. 8, the plate 30 is secured to the first part 20 by means of a support 36. Preferably, the plate 30 is also secured to the first part 20 along its edges 37 so as to form an enclosed cavity 38 underneath the depression 32.

As illustrated in the Figures, two tapes 40,42 are provided respectively for sealing the upper open portion of depression 32 and an aperture 44 provided in the bottom of the depression 32. Preferably, as illustrated, the free ends of the two tapes 40 and 42 are joined together.

In use, the two tapes 40 and 42 are simultaneously pulled out of the air inlet 26 so as to be peeled back from the depression 32, thereby exposing the open upper surface of depression 32 and the aperture 44 in the bottom of depression 32. When the user inhales through the outlet 28 of the inhaler, air is drawn into the air inlet 26, picking up powder 34 from the depression 32. Furthermore, a pressure difference is created between the channel above the plate 30 and the cavity 38 formed below the plate 30. In this way, air is drawn in the lower part of the air inlet 26 and through the aperture 44 in the bottom of the depression 32. This assists in ensuring that the powder contained in the depression 32 is transferred into the stream of air flowing through the inhaler.

By providing the depression 32 in a plate 30 housed within the inhaler as described above, the depression 32 is protected from being damaged and there is less chance of the depression 32 being accidentally opened, particularly by removal of the tape covering the aperture 44 in the bottom of depression 32. Furthermore, this arrangement allows additional air to be drawn into the system through the aperture 44 in the bottom of the depression 32 whilst ensuring that all air entering the system enters via the air inlet 26. In this way, there is less likelihood of the user accidentally blocking the aperture 44.

Figure 1:
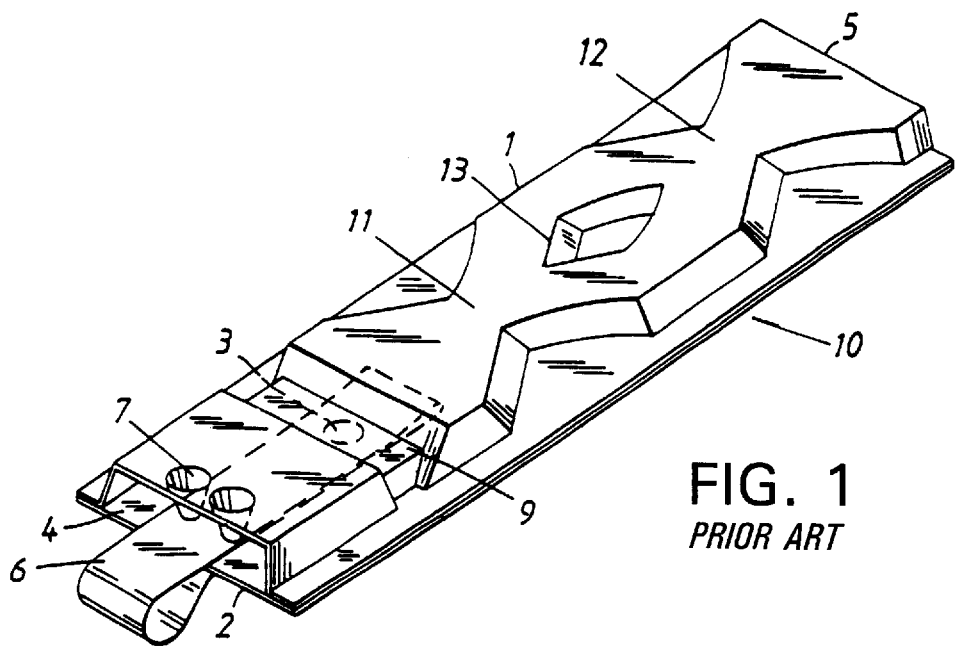
FIG. 1 illustrates a prior art inhaler.
Figure 2:
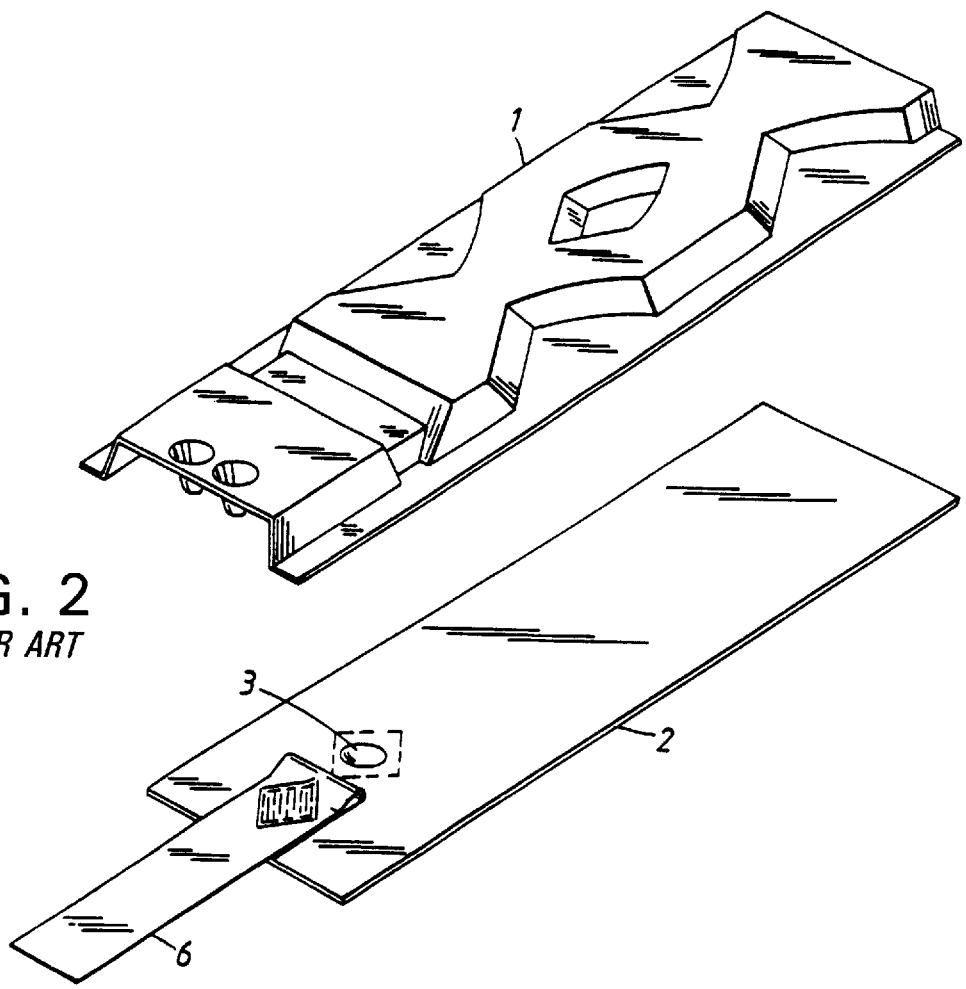
FIG. 2 illustrates the prior art inhaler of FIG. 1 separated into two parts.
Figure 3A:
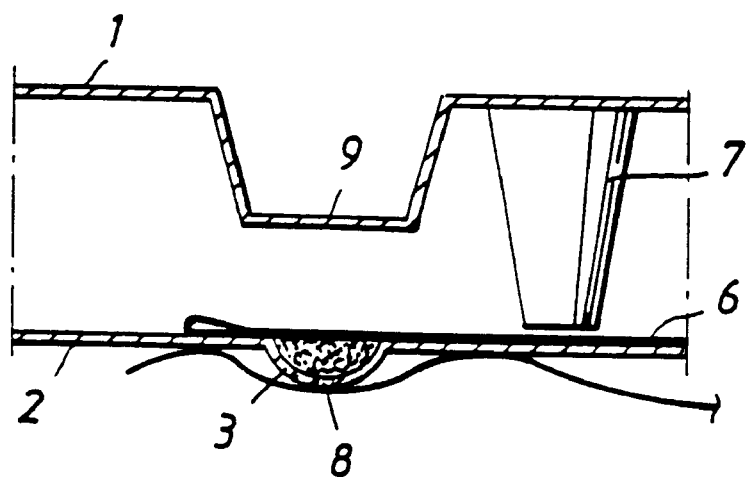
FIGS. 3a, 3b and 3c illustrate a cross-section of the prior art inhaler of FIG. 1.
Figure 3B:
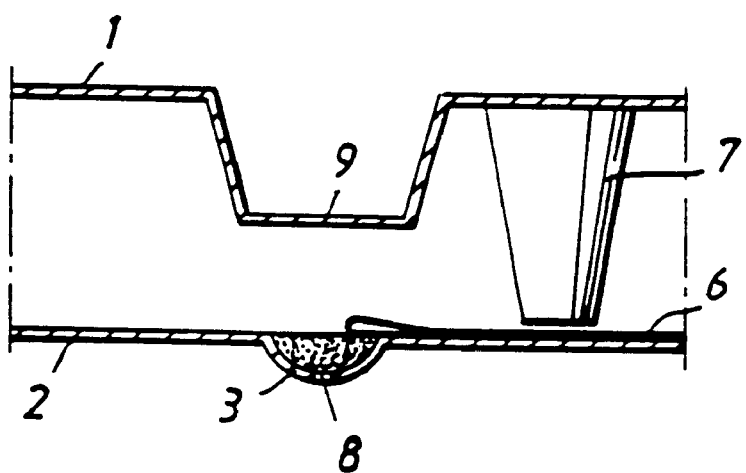
Figure 3C:
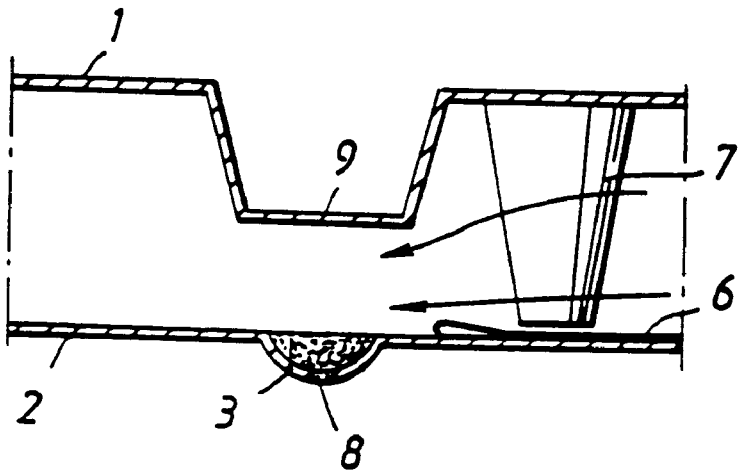
Figure 4:
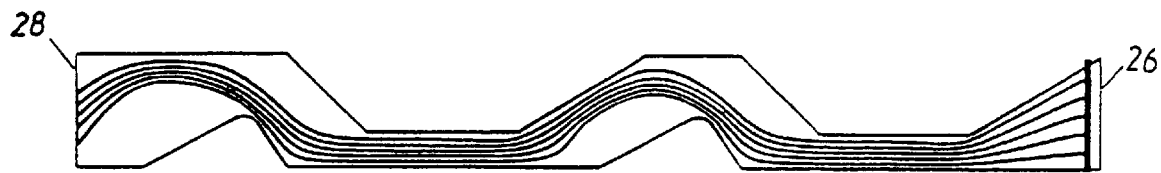
FIG. 4 illustrates the air flow path through one half of an inhaler.

FIG. 4 illustrates the streamlines which occur in one half of an inhaler where the angles of the walls of the inhalation channel have been optimized and a second divider has been introduced. Even though this inhaler gives excellent results, it is now realized that the impact of the airstream with walls of the channel downstream of the dividers gives little significant improvement in deagglomeration of powder.

Figure 9:
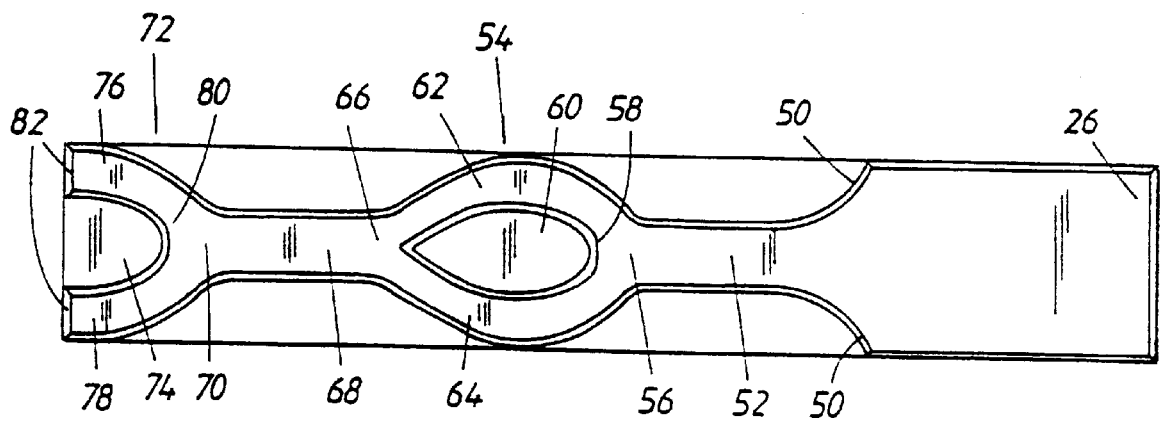
FIG. 9 illustrates the shape of the channel section through the inhaler of FIG. 5.

FIG. 9 illustrates a preferred shape of the walls of the channel resulting from the present invention and FIG. 11 illustrates the resulting streamlines.

Firstly, a general explanation of the flow of the air and powder will be given with reference to FIG. 9.

As explained before, air enters through the air inlet 26 and picks up powder 34 from the depression 32. The air powder mixture is then channelled by walls 50 into a first acceleration section 52. In the acceleration section 52, powder in the air/powder mixture, particularly the larger particles of powder, are brought into a stable axial flow before entering the first deagglomeration section 54. Opposite the section inlet 56 of the first deagglomeration section 54, a deagglomeration surface 58 of the first divider 60 is orientated perpendicular to the flow of the air/powder mixture as it passes through the section inlet 56. Preferably, and as illustrated, the deagglomeration surface 58 is generally planar, extends to the width of the section inlet 56 and is in alignment with the section inlet 56.

As illustrated in FIG. 11, the stream of air flows either side of the divider 60 with a smooth curved flow path. However, the particles of powder in the air stream, particularly the heavier particles of powder have sufficient axial momentum that they continue in a substantially straight line so as to impact with the deagglomeration surface 58. Upon impact, the particles break up into smaller constituent particles and rebound back into the air stream where they continue to flow with the air around the two side channels 62 and 64 of the first deagglomeration means 54.

At the section outlet 66 of the first deagglomeration section 54, the airflows of the two side channels 62 and 64 are recombined and enter into the second acceleration section 68.

In the second acceleration section 68, just as with the first acceleration section 52, the powder particles are once again brought into a stable flow with a strong axial momentum. At the section inlet 70 of the second deagglomeration section 72, once again the air flows smoothly either side of the second divider 74 along the two side channels 76 and 78. However, particles with sufficient axial momentum will leave the airstream and impact upon the deagglomeration surface 80 of the second divider 74. Just as with the deagglomeration surface 58 of the first divider 60, particles which impact the deagglomeration surface 80 will be broken down into smaller particles and rebound into the airstream to be carried down the side channels 76 and 78.

It will be appreciated that in the case of both the first and second deagglomeration sections, powder of sufficiently small size will be carried by the air flow around the respective divider 60, 74 without impacting upon the deagglomeration surface 58, 80. It will only be the larger particles which require deagglomeration that will have sufficient momentum to leave the airstream and impact with the deagglomeration surfaces 58 and 80. Thus, it will be appreciated that the acceleration section 68 will contain a higher proportion of fine particles than the accelerations section 52 and, therefore, a larger number of powder particles will be deflected around the second divider 74 without impacting its deagglomeration surface 80 than will be deflected around the divider 60 without impacting its deagglomeration surface 58. It will also be appreciated that the second deagglomeration section 72 acts to deagglomerate large particles which escaped deagglomeration by the first deagglomeration section 54. Particles which were deagglomerated by the first deagglomeration section 54 should merely flow around the second divider 74 without impacting upon its deagglomeration surface 80.

It is possible to provide third or subsequent deagglomeration sections similar to that of the first deagglomeration section 54. However, this results in an increase of the overall size of the inhaler, together with increased flow resistance through the inhaler for little improvement in deagglomeration.

As illustrated in FIG. 9, the second deagglomeration section 72 preferably comprises a section outlet made up of respective outlets from the side channels 76 and 78. By providing an outlet in this way, the size of the inhaler may be reduced with no adverse effect to its characteristics. Preferably, the section outlet 82 and, therefore, the inhaler outlet 28 is formed at a position where the air/powder mixture flow in the side channels 76 and 78 is substantially axial. This provides the best flow into the mouth of the user.

The preferred shape and size of the inhaler of FIG. 9 is best described with reference to FIGS. 10(a), (b), (c) and (d). These Figures illustrate the various parts of FIG. 9, but, rather than being annotated with reference numerals, are annotated with the preferred dimensions given in millimeters and, in one case, degrees. Where a number is prefixed by the letter R, the number refers to the radius of curvature of the indicated portion given in millimeters.

Figure 10A:
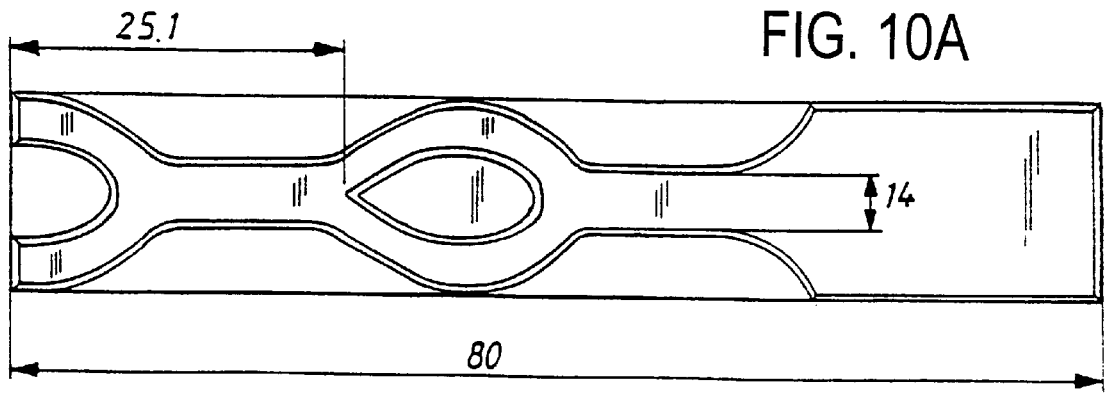

For the avoidance of doubt, FIG. 10(a) illustrates all of the channel illustrated in FIG. 9, FIG. 10(b) illustrates the lower channel wall of the inhaler as illustrated in FIG. 9 where the upper wall has identical dimensions, but symmetrically reversed, FIG. (c) illustrates the first divider 60 of the inhalation channel of FIG. 9 and FIG. 10(d) illustrates the second divider 74 of the inhalation channel of FIG. 9.

The inhalation channel defined by FIGS. 10(a) to (d) produces the streamlines illustrated in FIG. 11. As illustrated, there is virtually no disruption to the flow of air through the inhaler, such that, apart from powder being caused to impact with the deagglomeration surfaces of the dividers 60 and 74, powder will be smoothly carried through the inhaler such that deposition and retention of powder is minimized. Similarly, with a smooth disturbance free flow, the flow resistance is minimized, thereby making inhalation easier for the user and maximizing the transfer of his or her effort in inhalation into lifting, carrying and deagglomerating powder in the inhaler.

Figure 12:
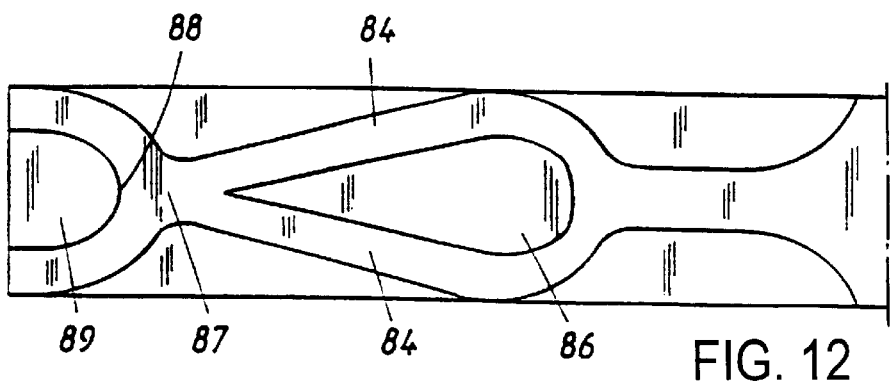
FIG. 12 illustrates the channel section of an alternative inhaler.

It will be appreciated that many of the dimensions illustrated in FIGS. 10(a) to (d) may be changed without departing from the present invention. Nevertheless, many of the dimensions are strongly interrelated such that changing one dimension may require many other dimensions to be changed similarly to achieve the effects described above and illustrated in FIG. 11. FIG. 12 illustrates an alternative embodiment where the side channels 84 of the first divider 86 themselves form an acceleration section. As illustrated, the two side channels 84 recombine at the second section inlet 87 so that there are two air flows at the section inlet 87 inclined relative to one another at a small angle. Nevertheless, the deagglomeration surface 88 of the second divider 89 is still substantially perpendicular to these two flows, since the angle between the two flows is relatively small. In the illustrated embodiment, the two flows enter the second deagglomeration section through a section inlet 87 with a single opening. However, it is also possible to provide two closely spaced separate openings, though this might make construction more difficult and, in some cases, promote retention downstream of the adjoining wall. In either case, the two air flows form a single air flow which projects powder towards the perpendicular deagglomeration surface 88.

The construction of an inhaler channel such as illustrated in FIGS. 9 and 10 or in FIG. 12 is dictated by many conflicting factors. For example, by introducing further deagglomeration sections, deagglomeration may be improved, but the size of the inhaler is increased, flow resistance is increased and retention is also likely to be increased. By increasing the cross-sectional area of the channel, the flow resistance can be reduced, but the flow velocity will also be reduced, such that it is difficult to achieve sufficient deagglomeration. Furthermore, the overall size of the inhaler is increased. By decreasing the cross-sectional area of the inhaler, the size of the inhaler would be reduced and the flow velocity would be increased, thereby potentially assisting in deagglomeration. However, flow resistance would be increased and there comes a point where, in small channels, it becomes extremely difficult to achieve a smooth undisturbed flow as illustrated in FIG. 11.

It is also possible to vary individual features of the inhaler. For instance, by shortening the lengths of the acceleration sections 52, 68 and 84, the inhaler size can be reduced, but at some point, the acceleration sections 52, 68 and 84 will become less effective in imparting the correct momentum to the carried particles. Similarly, the width of the acceleration sections 52 and 68 could be increased relative to the dividers 60 and 74, but, at some point, powder particles at the edges of the acceleration sections 52 and 68 will pass around the dividers 60 and 74 without impacting upon them. In contrast, if the dividers 60 and 74 are increased in width to correspond to the width of the acceleration sections 52 and 68, there will come a point when flow around the deagglomeration surfaces 58 and 80 of the dividers 60 and 74 will create an unacceptably large dead space from which powder particles will not rebound and retention will occur.

Thus, from the above, it will be appreciated that the present invention can be applied and can give rise to great advantages with a whole range of shapes of inhalation channel, the actual shape being determined by the start parameters for that channel. It will also be appreciated that, from the selection described above, the particular choice of parameters by which to optimize the inhalation channel and the inhaler as a whole would not be obvious.

As illustrated, the acceleration sections preferably have a cross-sectional area of the order of 16 $mm^2$ and, again as illustrated, are preferably formed as an approximate square. It is believed that the cross-sectional area could be increased to approximately 30 $mm^2$ before the inhaler became too large and particle speed too low and could be reduced to a cross-sectional area of approximately 9 $mm^2$ before the flow resistance became too great and the flow patterns too difficult to control. To optimize the deagglomeration of powder, the surface of each divider 60 and 74 facing its corresponding section inlet 56 and 70 should be substantially perpendicular to the air flow in the acceleration sections 52 and 60 across the entire width of the section inlets 56 and 70. This ensures that any large particle being carried in the flow in the acceleration sections 52 and 68 and which continues to travel generally in a axial direction will hit a divider 60, 74 in a generally perpendicular direction. This provides the maximum amount of energy to break up the particle. The rest of the shape of the side channels 62, 64, 76, 78 and the dividers 60 and 74 can then be determined to minimize the disruption and turbulence caused to the flow of air and powder.

Figure 13:
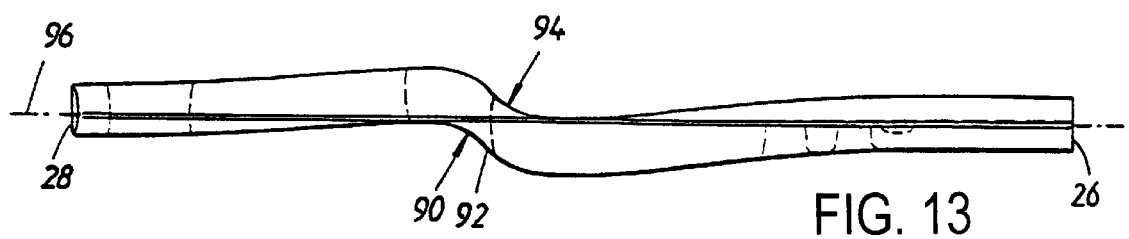
FIG. 13 illustrates schematically a side view of the inhaler of FIG. 6.

FIG. 13 illustrates schematically a side view of an inhaler such as described with reference to FIGS. 5 to 12. As is clear from FIG. 13, the inhaler extends in a generally first direction between the air inlet 26 and the outlet 28. Furthermore, the inhaler is of a generally flat construction, such that it extends in an elongate manner in a direction perpendicular to the first direction or, in other words, has a shallow extended rectangular or oval shape.

As illustrated in FIG. 13, unlike previous inhalers of this general form, the inhaler is not completely flat along its length, but, at position 90, is deflected downwards, such that it is displaced in a third direction perpendicular to both the first and second directions. This deflection or displacement provides a downwardly extended wall 92, which, in use, may be pressed against the lower lip of the user. In this way, the user can assuredly insert the inhaler into his or her mouth by the correct amount. Indeed, because of the shape of the inhaler, it will feel strange to insert the inhaler by less than the correct amount. In this way, the inhaler will be inserted with the outlet 28 over and clear of the user's tongue, rather than in a position where the user's tongue could still impede the flow of air/powder from the outlet into his or her lungs.

It is desirable that the inhaler retains its generally flat form. Therefore, at position 94, the inhaler is deflected back upwardly such that it is displaced or bent in a direction opposite to the third direction. In this way, the inhaler may have the required function and yet retain a pleasing gentle S-bend form.

In the preferred embodiment illustrated in FIG. 13, at position 90, the lower section has a radius of curvature of approximately 5 mm and the upper section a radius of curvature of approximately 8 mm and at the second position 94, the lower section has a radius of curvature of approximately 8 mm and the upper section a radius of curvature of approximately 5 mm.

Preferably, the downward bend occurs at approximately 30 mm from the outlet 28.

As also illustrated in FIG. 13, a plane 96 exists which passes within the inhaler. Shaping the inhaler with such a plane is highly advantageous, since, as illustrated, the inhaler can be more easily formed from only two moulded parts which are subsequently joined together along a flat surface.

This construction is particularly advantageous, since it does not require the use of a separate or special mouthpiece or any special indication on the inhaler. The inhaler comprises the same number of parts as an entirely flat inhaler, with no significant modification. Nevertheless, it provides a clear indication to the user as to how far it should be inserted into his or her mouth.

Figure 14:
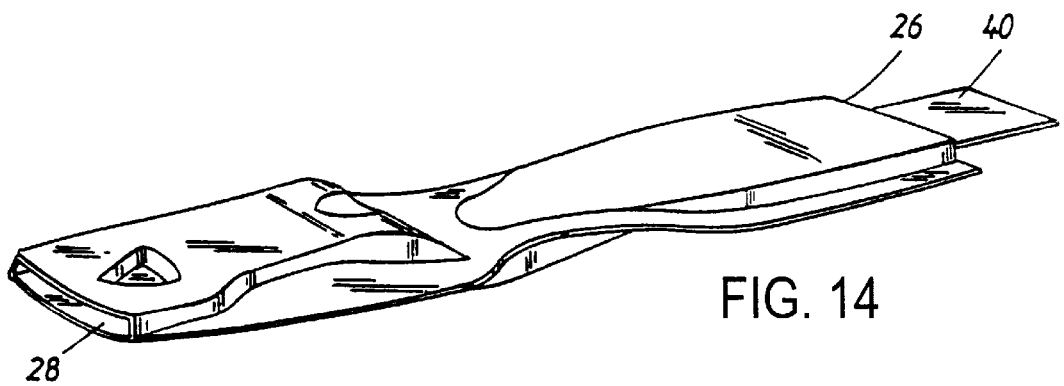
FIG. 14 illustrates an inhaler according to the present invention.

FIG. 14 illustrates an inhaler which could embody the various aspects of the present invention. It will be appreciated that the outer shape of the inhaler has no direct relevance on the present invention, though of course the design of an inhalation channel meeting the requirements of the present invention might necessarily put certain constraints on that outer shape.

What is claimed is:

1. An inhaler for administering powder by inhalation, the inhaler comprising:

structure defining a channel through which a stream of air may be drawn by inhalation of a user;

a powder dispenser for providing said powder in said stream of air for inhalation by the user;

said channel including a gradually converging, in a downstream direction, unobstructed acceleration section disposed within said channel, said acceleration section having an inlet portion, an elongated central portion, and an outlet portion forming a flow stream so as to constrict and accelerate the stream of air; and said channel including a deagglomeration section disposed within said channel downstream of said acceleration section, said deagglomeration section having a section inlet, a section outlet downstream of said section inlet, and a divider between said section inlet and said section outlet for dividing said stream of air to either side of said divider, wherein said divider has a surface opposite said section inlet and said surface is oriented at an angle substantially perpendicular to the flow of said stream of air passing through said section inlet.

2. An inhaler according to claim 1 wherein the surface of the divider extends over at least an area corresponding to a projection of the section inlet onto said divider.

3. An inhaler according to claim 1 wherein a central section of said surface is planar.

4. An inhaler according to claim 3 wherein said planar section extends over substantially all of the area corresponding to a projection of the section inlet onto said divider.

5. An inhaler according to claim 1 wherein the deagglomeration section includes, downstream of said surface, two pairs of opposed curved surfaces of similar shape that are shaped and spaced apart so as to provide stable airflow with gradual changes in direction and not restrict air flow in the stream of air through the inhaler.

6. The inhaler of claim 1, wherein said deagglomeration section is immediately adjacent said acceleration section within said channel.

7. The inhaler of claim 1, further comprising a second deagglomeration section disposed within said channel downstream of said deagglomeration section, said second deagglomeration section having a second section inlet, a second section outlet downstream of said second section inlet, and a second divider between said second section inlet and said second section outlet for dividing the stream of air either side of said second divider, wherein said second divider has a second surface opposite said second section inlet and said second surface is oriented at an angle substantially perpendicular to the flow of said stream of air passing through said second section inlet.

8. The combination of an inhaler as described in claim 1 and a powder wherein said powder contains a pharmaceutically active substance.

9. The combination of claim 8 wherein said substance is systemically active.

10. The combination of claim 8 wherein said substance is active in a bronchial area of the user.

11. The combination of claim 10 wherein said substance is used in treatment of a bronchial disease.

12. The combination of claim 11 wherein said substance is used in the treatment of asthma.

13. An inhaler for administering powder by inhalation, the inhaler comprising:

a channel through which a stream of air may be drawn by inhalation of a user;

a powder dispenser for providing said powder in said stream of air for inhalation by the user;

said channel including at least one deagglomeration section disposed within said channel, the at least one deagglomeration section having a section inlet, a section outlet downstream of said section inlet, and a divider between said section inlet and said section outlet for dividing said stream of air to either side of said divider, said divider having an impact surface substantially opposite said section inlet for dividing the air flow entering through said section inlet and affecting deagglomeration of powder in the air flow; and wherein the at least one deagglomeration section includes, downstream of said impact surface, two pairs of opposed curved surfaces of similar shape that are shaped and spaced apart so as to provide stable airflow with gradual changes in direction and not restrict air flow in the stream of air through the inhaler.

14. An inhaler according to claim 13 wherein said channel includes a substantially straight section joined to said section inlet.

15. An inhaler according to claim 13 wherein two deagglomeration sections are provided, the section outlet of one deagglomeration section being in fluid connection with the section inlet of the other deagglomeration section.

16. An inhaler according to claim 13 further comprising an inhaler outlet from which air and powder may be inhaled, the inhaler outlet comprising the section outlet of said at least one deagglomeration section.

17. The inhaler of claim 16, wherein the section outlet of the at least one deagglomeration section comprises two openings, one opening either side of said divider.

18. The inhaler of claim 17, wherein said two openings are positioned relative to said divider such that the air flow through said two openings are parallel.

19. A method of providing deagglomerated powder at an outlet of a channel guiding a stream of air, the channel including at least one deagglomeration section with a section inlet, a section outlet downstream of said section inlet, and a divider between said section inlet and said section outlet for dividing said stream of air either side of said divider, the method comprising:

providing powder in said channel upstream of said section inlet;

accelerating the stream of air by providing a gradually converging, in a downstream direction, unobstructed acceleration section upstream of said deagglomeration section inlet, said acceleration section having an inlet portion, an elongated central portion, and an outlet portion forming a flow stream so as to constrict and accelerate the stream of air; and providing a surface on said divider which is opposite said section inlet and which is oriented at an angle substantially perpendicular to the flow of the stream of air passing through said section inlet.

* * * * *